US012353379B1

(12) United States Patent
Lella et al.

(10) Patent No.: US 12,353,379 B1
(45) Date of Patent: Jul. 8, 2025

(54) ENHANCING DATA SETS TO CREATE DATA STORES

(71) Applicant: Amazon Technologies, Inc., Seattle, WA (US)

(72) Inventors: Vaibhav Lella, Mercer Island, WA (US); Fan Xiang, Seattle, WA (US); Sneha Avuthu, Lynnwood, WA (US); Ryan Hood, Bothell, WA (US); Varun Sembium Varadarajan, Redmond, WA (US); Parminder Bhatia, Seattle, WA (US); Arun Kumar Ravi, Kirkland, WA (US); Eric Chen, Seattle, WA (US); Arjun Mukhopadhyay, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 106 days.

(21) Appl. No.: 17/105,995

(22) Filed: Nov. 27, 2020

(51) Int. Cl.
G06F 16/22 (2019.01)
G06N 20/00 (2019.01)
G16H 10/60 (2018.01)

(52) U.S. Cl.
CPC .......... G06F 16/22 (2019.01); G06N 20/00 (2019.01); G16H 10/60 (2018.01)

(58) Field of Classification Search
CPC ....... G06F 16/22; G06F 16/283; G06N 20/00; G16H 10/60
See application file for complete search history.

(56) References Cited

U.S. PATENT DOCUMENTS

| | | | |
|---|---|---|---|
| 8,819,068 B1 * | 8/2014 | Knote | G06F 16/2282 707/790 |
| 10,565,475 B2 | 2/2020 | Lecue et al. | |
| 11,436,436 B2 | 9/2022 | Nakazawa | |
| 11,816,436 B2 | 11/2023 | Panuganty et al. | |
| 2005/0228818 A1 * | 10/2005 | Murthy | G06F 40/143 707/999.102 |
| 2007/0198564 A1 * | 8/2007 | Blackstone | G16H 10/60 |
| 2009/0112903 A1 * | 4/2009 | Liang | G06F 16/258 |
| 2009/0144295 A1 * | 6/2009 | Mion | G06F 16/00 |
| 2014/0282120 A1 * | 9/2014 | Sun | G06F 16/9558 715/760 |
| 2018/0101791 A1 * | 4/2018 | Viswanathan | G06N 20/20 |
| 2018/0210936 A1 * | 7/2018 | Reynolds | G06F 21/6227 |
| 2018/0314705 A1 * | 11/2018 | Griffith | G06F 16/185 |
| 2022/0164471 A1 * | 5/2022 | Braghin | G06F 16/213 |

* cited by examiner

*Primary Examiner* — Apu M Mofiz
*Assistant Examiner* — Farhad Agharahimi
(74) *Attorney, Agent, or Firm* — S. Scott Foster; Kowert, Hood, Munyon, Rankin & Goetzel, P.C.

(57) ABSTRACT

Data sets may be enhanced to create data stores. Request to create data stores may be received. As part of performing the request to create a data store, items stored in an extensible data format may be identified for machine learning enhancement. Machine learning models may be applied to generate additional data from data in the items. The additional data may be added to extend the items and store the extended items in a new data store.

20 Claims, 8 Drawing Sheets

ENHANCING DATA SETS TO CREATE DATA STORES

BACKGROUND

A variety of data ecosystems grow in various areas, including different industries and technological environments. In some environments, the volume of collected data may include data that is understood and supported by the systems that store it. In some environments, some portion of collected information may be hidden, disguised, or obscured by the form of the data such that the information such that systems cannot easily utilize the data.

While embodiments are described herein by way of example for several embodiments and illustrative drawings, those skilled in the art will recognize that embodiments are not limited to the embodiments or drawings described. It should be understood, that the drawings and detailed description thereto are not intended to limit embodiments to the particular form disclosed, but on the contrary, the intention is to cover all modifications, equivalents and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including, but not limited to.

It will also be understood that, although the terms first, second, etc. may be used herein to describe various elements, these elements should not be limited by these terms. These terms are only used to distinguish one element from another. For example, a first contact could be termed a second contact, and, similarly, a second contact could be termed a first contact, without departing from the scope of the present invention. The first contact and the second contact are both contacts, but they are not the same contact.

DETAILED DESCRIPTION OF EMBODIMENTS

Various techniques for implementing enhancing data sets to create data stores are described herein. Some data sets may be created from diverse data sources and stored together in a common data format. For example, healthcare data may be collected from different sources (e.g., labs, patients, doctors, insurance companies, etc.) and stored in a specified format, Fast Healthcare Interoperability Resources (FHIR). In such scenarios, some of the data provided by these data sources does not readily lend itself to further analysis for various, such as unstructured text data or other data in binary form, different document formats, image data, or audio data, among other examples. For systems that utilize data stored in data stores to support different features like search or machine-learning training and/or analysis, access to data that is provided, but not ascertainable for analysis, would improve the performance of such systems. For example, various features of input data in a machine learning training and/or evaluation system (e.g., to classify, predict, etc.) may be enhanced by the inclusion of additional attributes of data located in the provided, yet inaccessible data. Therefore, in various embodiments, techniques for enhancing data sets to create data stores may be implemented to discover the hidden information in the provided data sets and add to accessible data to improve the performance of systems that can benefit from the additional information.

Figure 1:
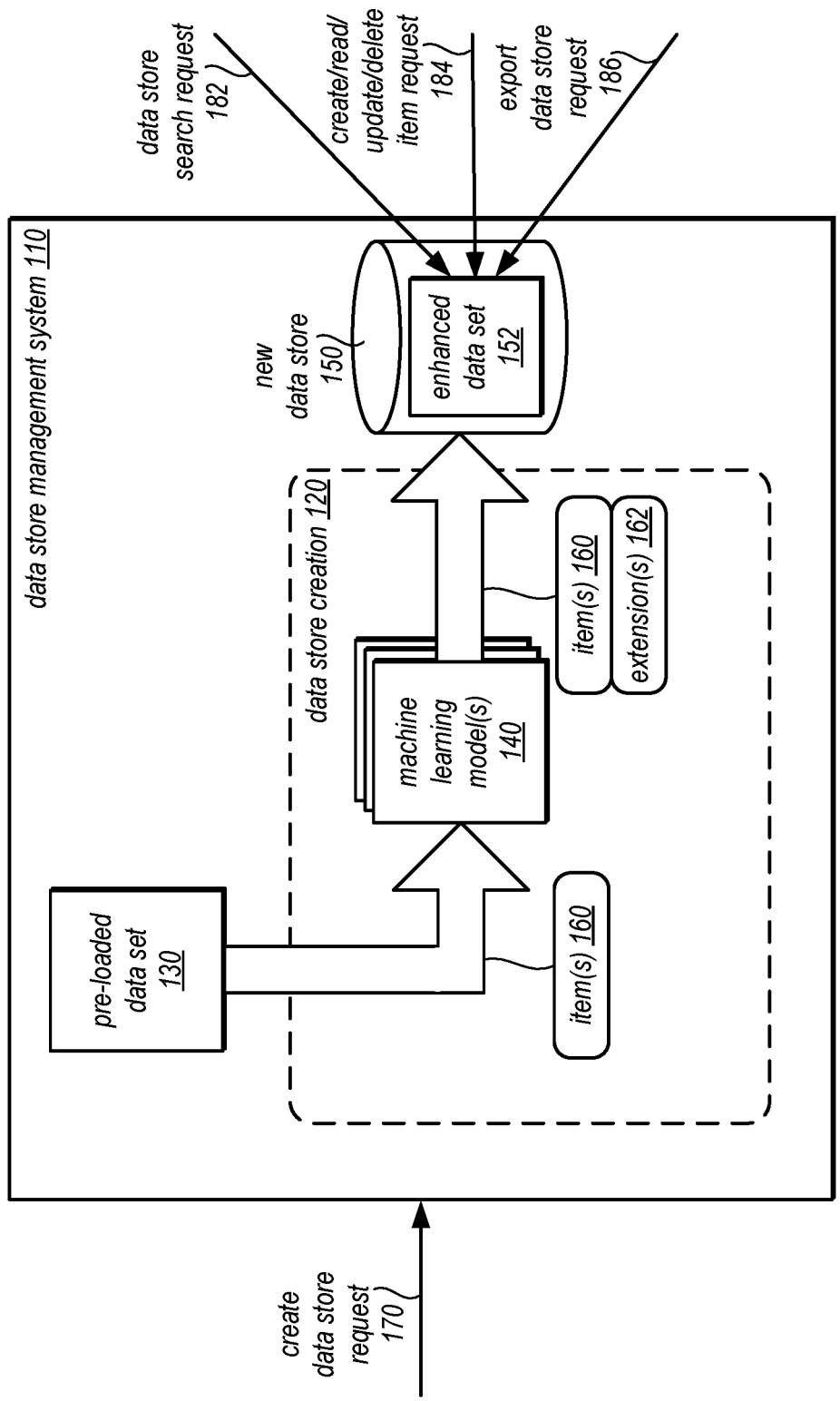
FIG. 1 illustrates a logical block diagram of enhancing data sets to create data stores, according to some embodiments.

FIG. 1 illustrates a logical block diagram of enhancing data sets to create data stores, according to some embodiments. Data store management system 110 may be implemented as a standalone system, application, or service, which may create and manage data stores on behalf of users or applications, or in some embodiments, be implemented as a private or publicly available service for a provider network (as discussed in detail below with regard to FIG. 2). Data store management system 110 may perform various tasks to create and management data stores, including techniques to enhance data for the created data stores using machine learning techniques. For example, as illustrated in FIG. 1, a request to create a data store 170 may be received, in some embodiments. The request 170 may, in various embodiments, specify or indicate using a pre-loaded data set, such as pre-loaded data set 130. In this way, various features of data store management system can be quickly evaluated or ascertained by users to determine whether, for example, to utilize data store management system to create data stores for other systems or applications. Pre-loaded data set 130 may be a synthetically created data set, in some embodiments, in order to provide realistic data for performing various operations without requiring a user to upload data in order to utilize data management system. For example, for applications in sensitive data environments, such as financial or medical systems, pre-loaded data set 130 may offer an alternative to provide a "one-click" experience, so that data store management system 110 can be quickly and easily evaluated. In some embodiments, data store management system 110 may utilize various data set generation tools or applications according to a respective domain of knowledge for different data stores. Record generators of synthetic information for medical data stores, such as FHIR, may be implemented to provide test data without the potential for data loss or other scenarios involving sensitive information while evaluating data store management system 110. For any sensitive data added to or otherwise handled by data store management system 110, all appropriate techniques and guidelines to comply with the appropriate regulation and privacy protection schemes may be applied by data store management system 110.

Data store creation 120 may, among other operations, take pre-loaded data set 130 and evaluate the respective item(s)

160 of the data set. For some items, as discussed in detail below with regard to FIGS. 3, 6, and 7, various machine learning models may be applied to determine attributions or other information that was otherwise hidden/referenced in a portion of item(s) 160. For example, unstructured text stored in a binary format may be evaluated using machine learning model(s) 140 to determine various attributes or features of the text. When additional data is generated, the additional data may be added as one or more extensions 162 to item(s) 160. Thus, in various embodiments, items 160 may, in various embodiments, be stored in an extensible data set, that supports adding additional information to refer to items 160 (or portions thereof) either directly in the items (e.g., as additional fields, statements, or other text/values) or by linked or associated data objects or files that describe or point to the portions of items 160 which they extend. For example, FHIR supports extensions to items (e.g,. resources), such as DocumentReference (which may include various metadata describing additional documents or other data, including notes, image files, non-standard text formats, binary data, digital representations of text, other repositories or records, etc.) by allowing for extension information to be written into an item (e.g., into a JSON document that includes the item adding extension fields and information).

The enhanced items 160 may then be stored as part of enhanced data set 152 in new data store 150, in various embodiments. Data store management system 110 may support various other interactions with the enhanced data set, as discussed in detail below with regard to FIGS. 4 and 5, including data store search requests 182, create, read, update, or delete item requests 184, and export data store request 186, in some embodiments. These requests may have access to and utilize the additional data in extensions 162 in enhanced data set 152, in various embodiments.

The previous description of a data store management system in FIG. 1 is a logical illustration and thus is not to be construed as limiting as to the architecture for implementing a data lineage system.

This specification begins with a general description of a provider network that implements a data storage management service. Then various examples of the data store management service including different components/modules, or arrangements of components/module that may be employed as part of implementing enhancing data sets to create data stores are discussed. A number of different methods and techniques to implement enhancing data sets to create data stores are then discussed, some of which are illustrated in accompanying flowcharts. Finally, a description of an example computing system upon which the various components, modules, systems, devices, and/or nodes may be implemented is provided. Various examples are provided throughout the specification.

Figure 2:
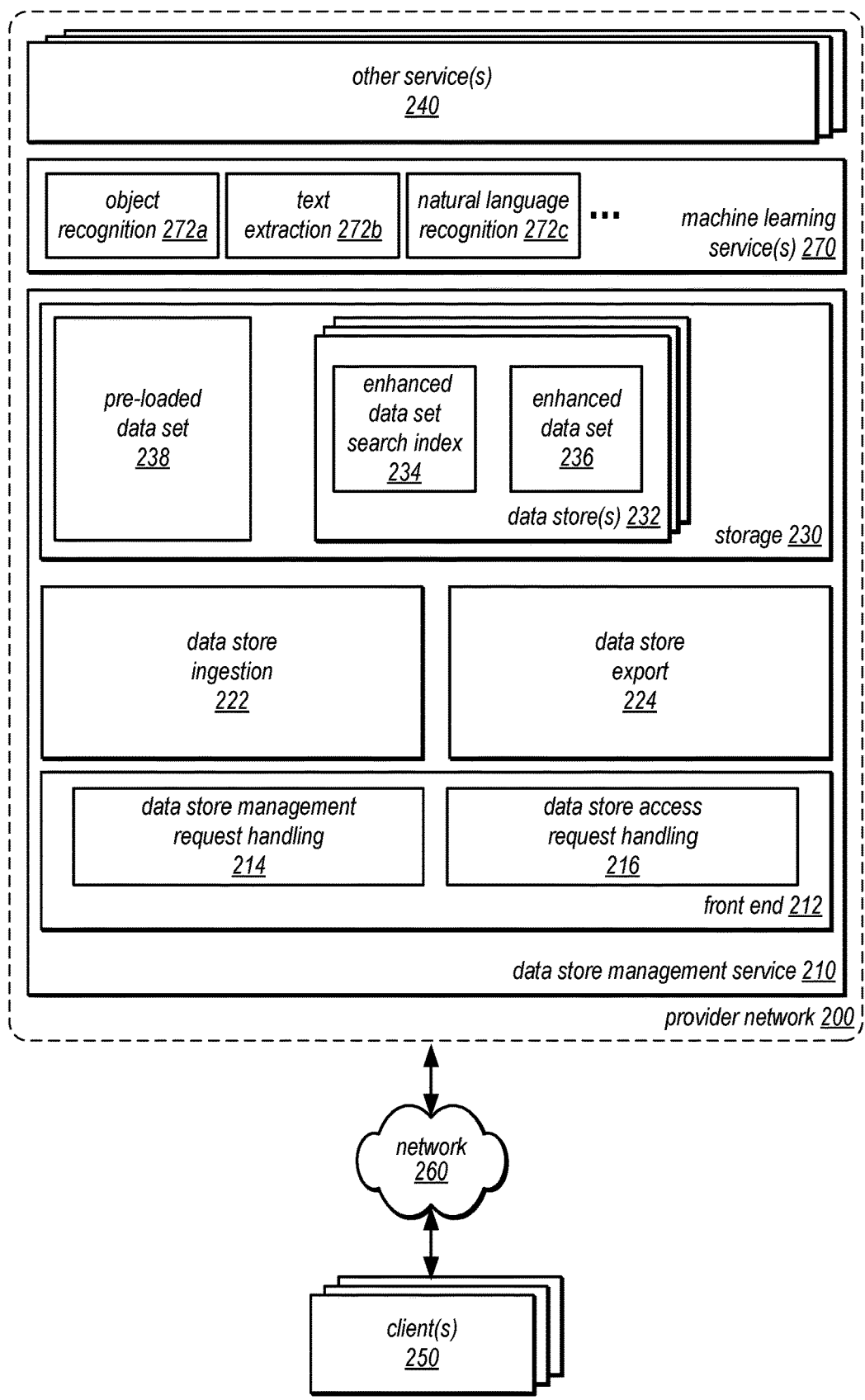
FIG. 2 is a logical block diagram illustrating a provider network implementing a data store management service that implements enhancing data sets to create data stores, according to some embodiments.

FIG. 2 is a logical block diagram illustrating a provider network implementing a data store management service that implements enhancing data sets to create data stores, according to some embodiments. Provider network 200 may be a private or closed system or may be set up by an entity such as a company or a public sector organization to provide one or more services (such as various types of cloud-based storage) accessible via the Internet and/or other networks to clients 250. Provider network 200 may be implemented in a single location or may include numerous data centers hosting various resource pools, such as collections of physical and/or virtualized computer servers, storage devices, networking equipment and the like (e.g., computing system 1000 described below with regard to FIG. 8), needed to implement and distribute the infrastructure and storage services offered by the provider network 200.

For example, the provider network 200 (which may, in some implementations, be referred to as a "cloud provider network" or simply as a "cloud") refers to a pool of network-accessible computing resources (such as compute, storage, and networking resources, applications, and services), which may be virtualized or bare-metal. The provider network 200 can provide convenient, on-demand network access to a shared pool of configurable computing resources that can be programmatically provisioned and released in response to customer commands. These resources can be dynamically provisioned and reconfigured to adjust to variable load.

The provider network 200 can be formed as a number of regions, where a region is a separate geographical area in which the cloud provider clusters data centers. Each region can include two or more availability zones connected to one another via a private high speed network, for example a fiber communication connection. An availability zone (also known as an availability domain, or simply a "zone") refers to an isolated failure domain including one or more data center facilities with separate power, separate networking, and separate cooling from those in another availability zone. Preferably, availability zones within a region are positioned far enough away from one other that the same natural disaster should not take more than one availability zone offline at the same time. Customers can connect to availability zones of the provider network 200 via a publicly accessible network (e.g., the Internet, a cellular communication network). Regions are connected to a global network which includes private networking infrastructure (e.g., fiber connections controlled by the cloud provider) connecting each region to at least one other region. The provider network 200 may deliver content from points of presence outside of, but networked with, these regions by way of edge locations and regional edge cache servers. This compartmentalization and geographic distribution of computing hardware enables the provider network 200 to provide low-latency resource access to customers on a global scale with a high degree of fault tolerance and stability.

In some embodiments, provider network 200 may implement various computing resources or services, such as a data store management service 210, machine learning service(s) 270, as well as other service(s) 240, which may include a virtual compute service, data processing service(s) (e.g., map reduce, data flow, and/or other large scale data processing techniques), data storage services (e.g., object storage services, block-based storage services, or data warehouse storage services) and/or any other type of network based services (which may include various other types of storage, processing, analysis, communication, event handling, visualization, and security services not illustrated). The resources required to support the operations of such services (e.g., compute and storage resources) may be provisioned in an account associated with the cloud provider, in contrast to resources requested by users of the provider network 200, which may be provisioned in user accounts.

In various embodiments, the components illustrated in FIG. 2 may be implemented directly within computer hardware, as instructions directly or indirectly executable by computer hardware (e.g., a microprocessor or computer system), or using a combination of these techniques. For example, the components of FIG. 2 may be implemented by a system that includes a number of computing nodes (or simply, nodes), each of which may be similar to the computer system embodiment illustrated in FIG. 8 and described below. In various embodiments, the functionality of a given system or service component (e.g., a component of data storage service 230) may be implemented by a particular node or may be distributed across several nodes. In some embodiments, a given node may implement the functionality of more than one service system component (e.g., more than one data store component).

Data store management service 210 may implement various features for users or client applications to create, update, access, export, utilize or otherwise management a data store, in some embodiments. As discussed above with regard to FIG. 1, some data use cases may utilize multiple different access and utilization features, which data store management service 210 may provide. Moreover, as the performance of systems that rely upon the stored data may be improved using enhanced data, data store management service 210 may implement various techniques to enhance data with machine-learning based techniques.

Data storage management service 210 may implement a front end 212, which may include various interfaces, such as programmatic interfaces (e.g., one or more Application Programming Interfaces (APIs)), command line interfaces, and/or graphical user interfaces (e.g., web-based consoles). Front-end 212 may implement various request handling features to active components in a control plane and data plane for data store management service 210. For example, data store management request handling 214 may support various features, such as creating a data store (discussed in detail below with regard to FIGS. 3 and 6), exporting a data store (discussed in detail below with regard to FIG. 5), deleting a data store, and/or upgrading or modifying resource allocations for the data store (e.g., increasing the size and/or number of service computing resources used to store and/or handle access requests to the data store), among other management requests. Front end 212 may also implement data store access request handling, in some embodiments, which may support various types of requests to access items in data stores. For example, as discussed in detail below with regard to FIG. 4, search requests, create item requests, read item requests, update item requests, and/or delete item requests may be dispatched and completed by data store access request handling 216, in some embodiments.

Data store management service 210 may implement various workflows or pipelines of operations to ingest data for a data store, such as data store ingestion 222, and export data from a data store, such as data store export 224. For example, as discussed in detail below with regard to FIG. 3, data store ingestion may obtain data from sources, such as pre-loaded data set 238 or other sources, identify, generate, and include additional data to enhance items, update search indexes for the data store, such as data set search index, and store items in an enhanced data set 236 in a created data store 232, in various embodiments. As discussed in detail below with regard to FIG. 5, data store export 224 may implement various workflows or pipelines of operations to export enhanced data sets 236 from a data store 232 to a target system, location, and/or format, in some embodiments.

In various embodiments, data store management service may implement storage 230, which may provide a storage tier, system, or service for create data stores. In some embodiments, storage 230 may be implemented across one or more other service(s) 240, such as various types of databases, index stores, object-based stores, and/or other storage technologies which data store management service 210 may treat as the back-end data store for data stores 232, including enhanced data set search index 234 and enhanced data set 236, managed by data store management service 210. Other data store management service 210, such as a pre-loaded data set 238, as discussed above with regard to FIG. 1, may also be implemented, in some embodiments.

Machine learning service(s) 270 may be implemented as part of a provider network 200 to perform various tasks based on machine-learning models, in some embodiments. For example, object recognition tasks 272 may be performed to recognize and/or classify object in provided image data, text extraction 27b may be performed to extract text from given documents (e.g., text in images or Portable Document Format (PDF)), and natural language recognition 272c (e.g., to recognize and label features of unstructured text), among other machine learning-based tasks. In at least some embodiments, machine learning services 270 may provide analysis for specific domains of knowledge, such as legal, medical, various specific scientific fields, and so on. For example, in some embodiments, one machine learning service 270 may extract medical information form unstructured text to identify various features, such as medical conditions, medications, dosages, strengths, and frequencies from a variety of sources like doctor's notes, clinical trial reports, and patient health records. Such a machine learning service could also identify the relationship among the extracted medication and test, treatment and procedure information for easier analysis. For example, the service identifies a particular dosage, strength, and frequency related to a specific medication from unstructured clinical note. Such features may be utilized by data stores for a specific knowledge domain, such as FHIR data stores discussed above, to provide attributes or other information to enhance data sets, as discussed above with regard to FIG. 1 and below with regard to FIGS. 3, 6, and 7, in some embodiments.

Generally speaking, clients 250 may encompass any type of client configurable to submit network-based requests to provider network 200 via network 260, including requests for data store management service 210 (e.g., a request to create a data store, search a data store, create/read/update/delete an item from a data store, export a data store, and so on). For example, a given client 250 may include a suitable version of a web browser, or may include a plug-in module or other type of code module configured to access a management console for front end 212. Alternatively, a client 250 may encompass an application to access or utilize data store management service 210. In some embodiments, such an application may include sufficient protocol support (e.g., for a suitable version of Hypertext Transfer Protocol (HTTP)) for generating and processing network-based services requests without necessarily implementing full browser support for all types of network-based data. That is, client 250 may be an application configured to interact directly with provider network 200. In some embodiments, client 250 may be configured to generate network-based services requests according to a Representational State Transfer (REST)-style network-based services architecture, a document- or message-based network-based services architecture, or another suitable network-based services architecture. Although clients 250 are illustrated as external to provider network 200, in some embodiments clients of different services, like data store management service 210, can be implemented within provider network 200 (e.g., implemented on a resource of other service(s) 230, such as virtual compute instance).

Clients 250 (or external data processors 270) may convey network-based services requests (e.g., requests to interact with data lineage service 220 to create a data flow model) to and receive responses from provider network 200 via network 260. In various embodiments, network 260 may encompass any suitable combination of networking hardware and protocols necessary to establish network-based-based communications between clients 250 (or external data processors 270) and provider network 200. For example, network 260 may generally encompass the various telecommunications networks and service providers that collectively implement the Internet. Network 260 may also include private networks such as local area networks (LANs) or wide area networks (WANs) as well as public or private wireless networks. For example, both a given client 250 and provider network 200 may be respectively provisioned within enterprises having their own internal networks. In such an embodiment, network 260 may include the hardware (e.g., modems, routers, switches, load balancers, proxy servers, etc.) and software (e.g., protocol stacks, accounting software, firewall/security software, etc.) necessary to establish a networking link between given client 250 (or external data processor 270) and the Internet as well as between the Internet and provider network 200. It is noted that in some embodiments, clients 250 (or external data processors 270) may communicate with provider network 200 using a private network rather than the public Internet.

Figure 3:
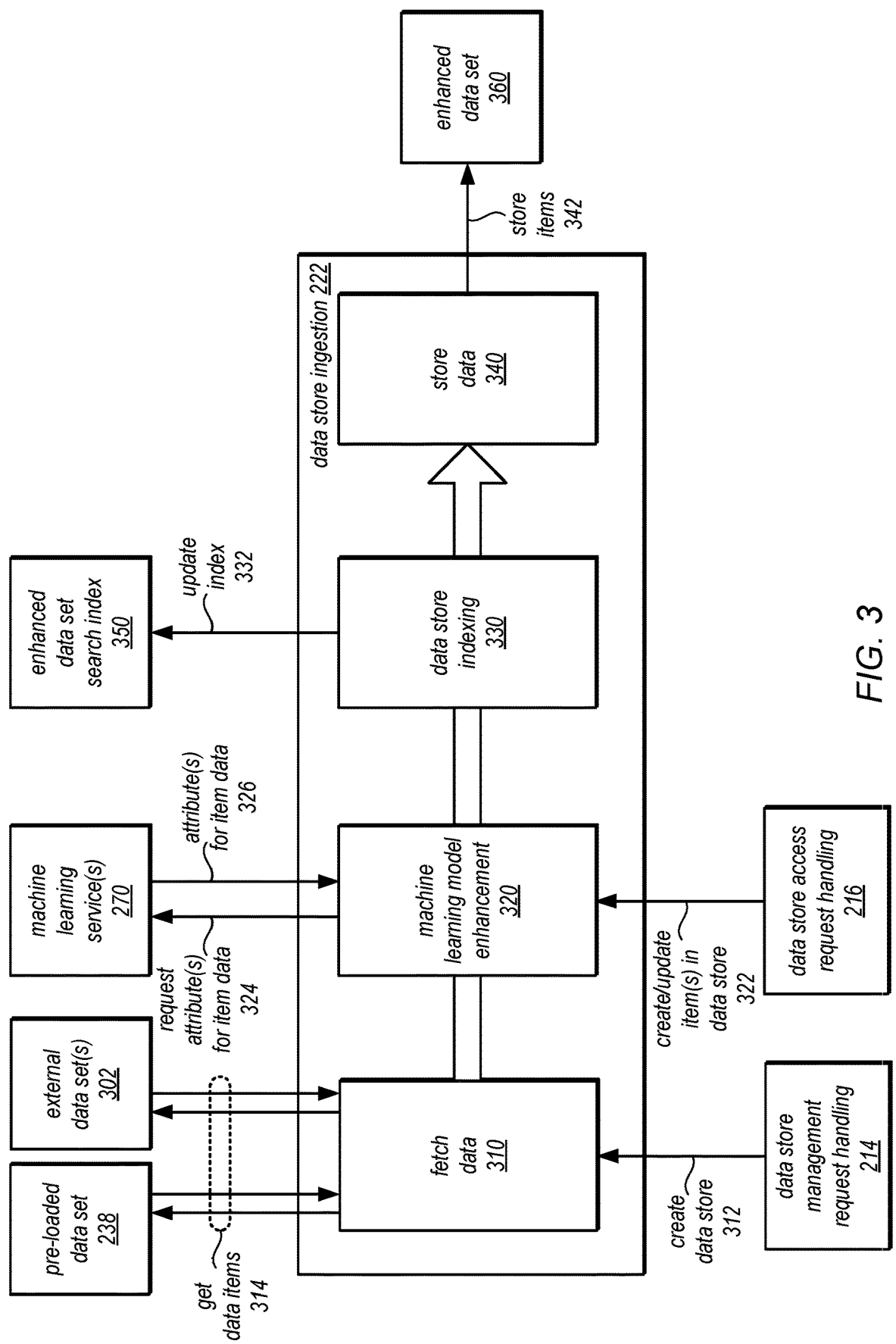
FIG. 3 is a logical block diagram illustrating data store ingestion, according to some embodiments.

Data enhancement may be handled as part of ingestion pipeline or workflow stages, in various embodiments. FIG. 3 is a logical block diagram illustrating data store ingestion, according to some embodiments. Data store ingestion 222 may support requests to create a data store 312 via data store request handling management 214. A creation request 312 may include various features, as discussed above. For example, a creation request may describe a version for the data store, such as a version of the specification or other schema that describes the extensible data format (e.g., FHIR). In some embodiments, different versions of the specification may be specified so that the data may be obtained in and stored in that version of the specification or schema for the extensible data format (e.g., FHIR v. 4.0). Data store creation requests may include a name or other identifier for the data store, in some embodiments. In some embodiments, data store creation requests may include an option specify the data store to be created with pre-loaded data (e.g., instead of an empty data store which may be populated via later request). For example, a parameter or other feature of the creation request may indicate to use a default pre-loaded data set or select from multiple available pre-loaded data sets.

Creation request 312 may trigger operations or tasks via different stages of data store ingestion 222. For example, fetch data stage 310 may get items from a pre-loaded data set 238 (as discussed above), external data set(s) 302 (e.g., hosted in another service or external to provider network 200), in some embodiments. Fetch data 310 may implement the various features, protocols, connections, or other operations to connected to and get 314 data items to create the data store. Fetch data 310 may implement batch or serialized techniques for getting items in groups or individually, in some embodiments. In some embodiments, fetch data 310 may store items in an intermediate data store (e.g., an intermediate database table, such as a non-relational database or document store), which may trigger the performance of other ingestion techniques, such as machine learning model enhancement 320, data store indexing 330, and so on. In some embodiments, individual items may be made available when placed in this intermediate data store for read, update, and/or delete item requests, as discussed below with regard to FIG. 4. For example, requests to create or update items in the data store 322, which may be handled by data store access request handling, may be written to the intermediate data store, which may trigger other ingestion stages, such as model enhancement 320, data store indexing 330, and so on. Thus, in some embodiments, enhanced data set search index 350 may be considered to be eventually consistent with enhanced data set 360 (as items may be available in enhanced data set 360 before they are available in enhanced data set search index 350). Similarly, some items that may be eventually enhanced at machine learning model enhancement 320 but may be made available in an unenhanced form when fetched (e.g., from the intermediate table).

In various embodiments, machine learning model enhancement 320 stage may be implemented to identify and request machine learning model execution for items to generate additional data, as well as update the items to add the additional data, as discussed in detail below with regard to FIGS. 6 and 7, in some embodiments. For example, machine learning model enhancement 320 may recognize fields, values, attributes, or tags, which may identify data for enhancement. As discussed below, feature such as unstructured text, or other indications, like analyzable content, like links to images, documents, or other data objects, may be recognizable according to file extension, location, or various other characteristics as susceptible to enhancement by machine learning techniques. In some embodiments, the machine learning techniques for enhancement may be specified as part of the creation request, and therefore an evaluation to identify for the specified machine learning techniques may be carried out. in some embodiments, machine learning model enhancement 320 may utilize multiple machine learning models may be executed in order to enhance data and may determine a workflow or plan of execution for the different services, execute requests according to the determined workflow and provide the output received from one service as input data in a form appropriate for invoking another service, in some embodiments.

Machine learning model enhancement stage 320 may submit requests for attributes for item data 324, using data taken from items (e.g., unstructured data, links, paths, or other identifying information for machine learning service(s) 270 to obtain data, etc.) and receive back attribute(s) for item data 326. As discussed above with regard to FIG. 1 and below with regard to FIGS. 6 and 7, machine learning model enhancement 320 may modify, update, or otherwise add to items to include the additional attribute(s) for item data.

In various embodiments, enhanced items may then be provided to data store indexing 330, which may perform various indexing techniques to update 332 one or more indexing data structures in enhanced data set search index 350. For example, different attribute values may be searchable, therefore different respective indexing structures (e.g., b-trees), which index on each attribute may be updated when such attributes are found in the items or additional item data.

Data store ingestion 222 may implement store data 340 stage, in various embodiments, which may store items 342 in enhanced data set 360. For example, one or more files or data objects may be accessed and/or written to include new items, updated to add new files with new items, or otherwise sent new items to be included in the enhanced data set for future access or export, as discussed below.

Although not illustrated, various stages of data store ingestion 222 may update corresponding state information for the request, which may be used to respond or indicate (e.g., via an interface) when the export request is complete. For example, an interface may display or provide a status indication of creation request, which may indicate "inprogress" or "complete", for instance. In some embodiments, an indication or other notification of when a data store is completed may be sent (e.g., to a requesting client application).

Figure 4:
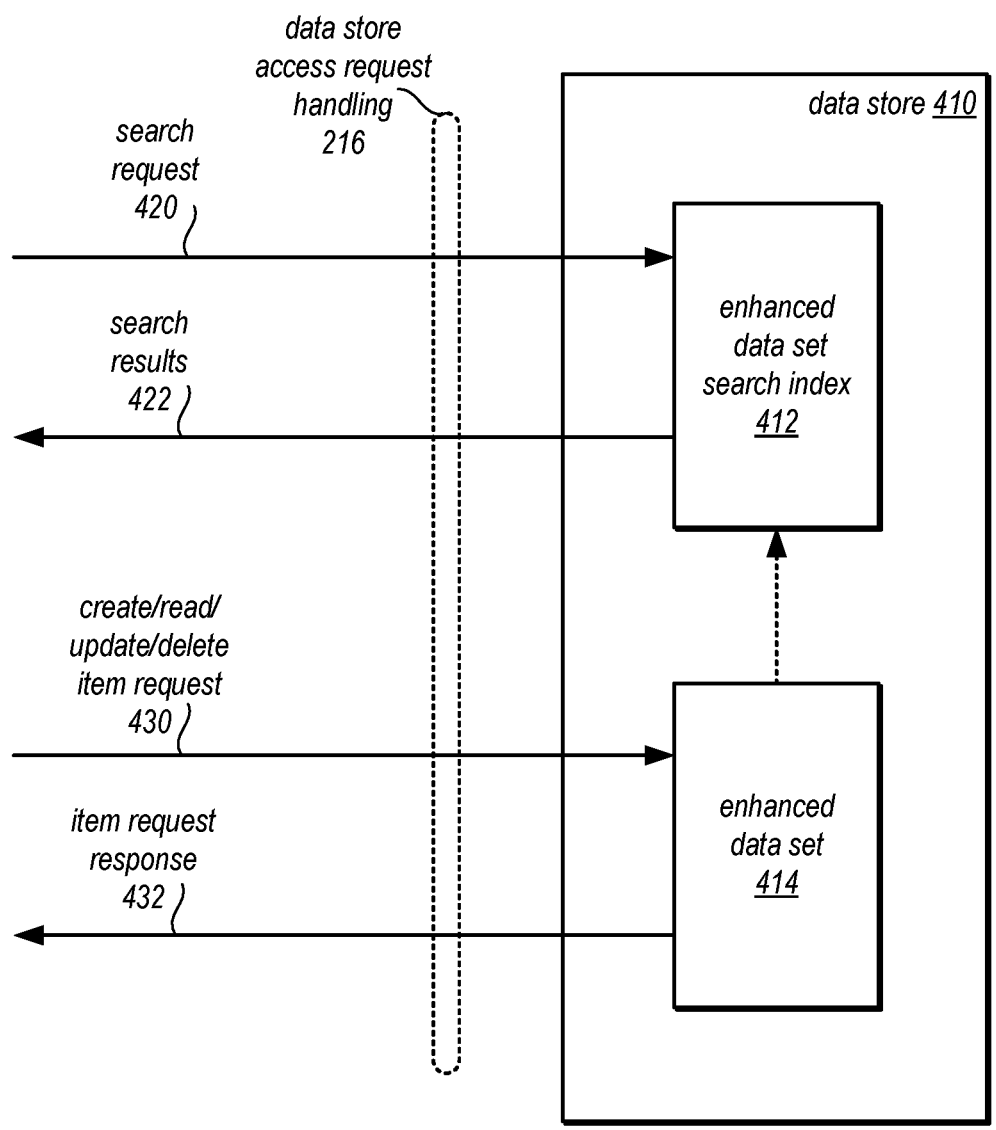
FIG. 4 is a logical block diagram illustrating data store access request handling, according to some embodiments.

Data store management service 210 offers different capabilities for access enhanced data. As discussed above with regard to FIGS. 1 and 3, different interfaces may be implemented to support different types of access request using search indexes as well as accessing individual items. FIG. 4 is a logical block diagram illustrating data store access request handling, according to some embodiments. Data stores access request handling 216 may support various interface requests, such as programmatic requests (e.g., APIs), command line commands, and/or graphical user interface (e.g., web-based console) requests to access a created data store, such as data store 410. Data store access request handling 216 may dispatch these requests to the appropriate storage 230 systems to respond to the access request.

For example, in some embodiments, search request 420 may be handled by data store access request handling 216 and dispatched to perform the search request using data set search index 412. Search request 420 may include various features, such as a data store identifier or name, a specific type of item (e.g., a FHIR resource type), comparators for time created, stored or updated based on a given date, data types (e.g., integer, Boolean, string, decimal, URI, binary, date, time, etc.), quantities, URIs, references, strings, date/times, various comparators (e.g., missing, exact, contains, not, text, identifier, in below, equals, not equals, greater than, less than, greater than or equals, less than or equals, after or before, above, etc.), search result or control features (e.g., filter, sort, score, count, summary, include, etc.), specification specific data types (e.g., FHIR data types like, annotation, coding, money, period, range, ratio, sample data, signature, etc.), among other features. Search request 420 may return, include or be directed to additional data, such as various added attributes to items, in various embodiments.

Data set search index 412 may, for instance be an Elasticsearch index or other text search-enabled index. Data set search index 412 may support various queries on the features discussed above, utilizing various internal data structure (e.g., indexes) and/or other mappings to return search results 422.

In some embodiments, individual items may be accessed. For example, a request to create an item, read an item, update an item or delete an item 430 may be dispatched by data store access request handling 216 to one or more hosts storing a storage or other engine for access enhanced data set 414. For example, a create request may be a request to create a new item to add to an existing enhanced data set and include features that identify the data store and item information in the data extensible format (e.g., specified according to FHIR). Data store access request handling 216 may support the create request by adding the item to enhanced data set 414. Similarly, an update request may identify the data store, item (e.g., by identifier), and/or field or other attributes to update, in some embodiments. In some embodiments, create and/or update requests may trigger various ingestion features, such as machine learning enhancement. In some embodiments, data store access request handling 216 may support read requests, which may specify an item (e.g,. a FHIR resource) by an identifier for the data store and resource. Data store access request handling 216 may also support delete item requests, which may identify by identifier the data store and item to delete from enhanced data set 414. Different respective responses for item requests 432 may be returned (e.g., acknowledgement or requested item data).

Figure 5:
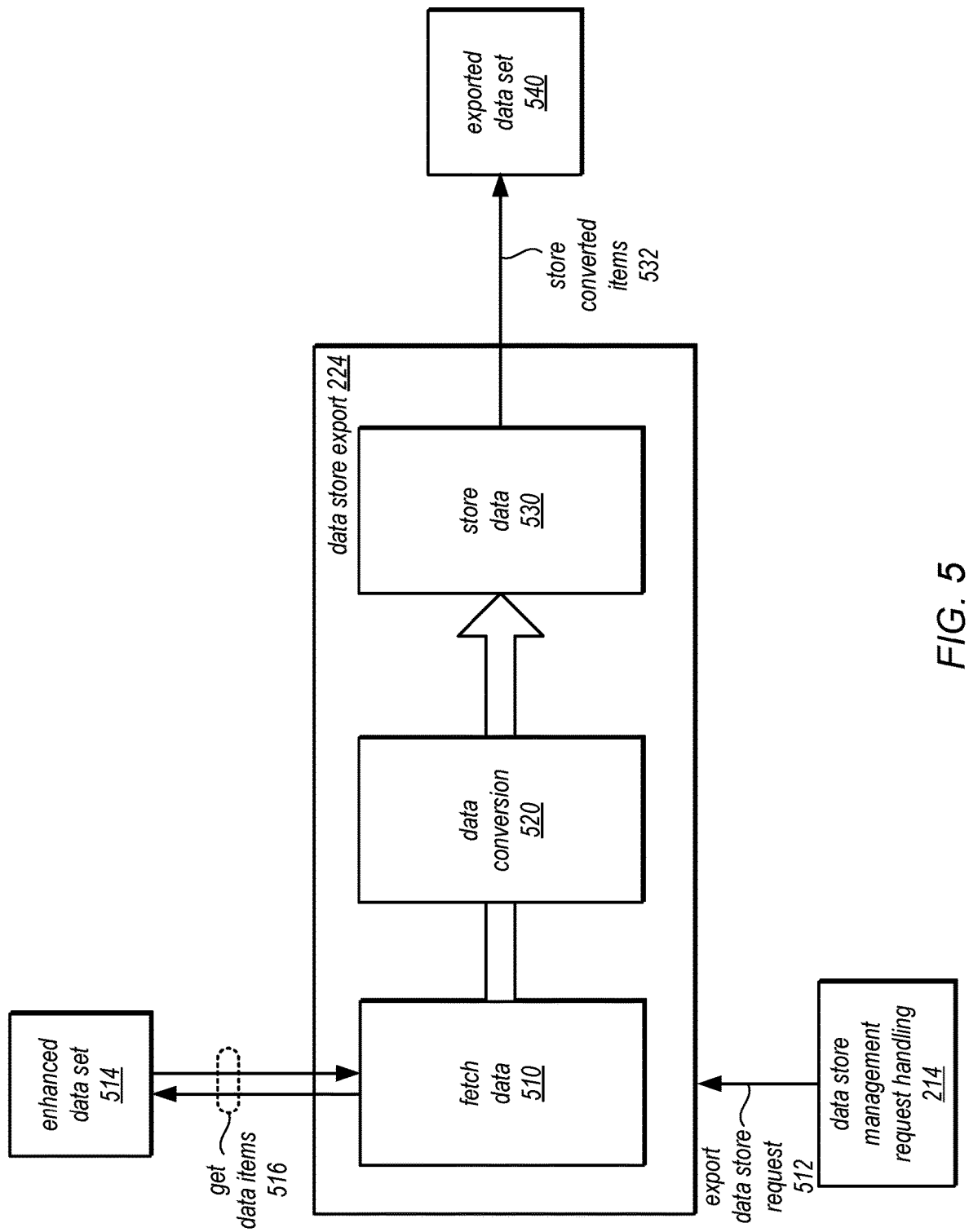
FIG. 5 is a logical block diagram illustrating data store export, according to some embodiments.

Enhancements to the data set stored in the data store may support may improve the performance of other system that rely upon or use the data set. Therefore, data store management service 210 may, in various embodiments, offer the capability to export enhanced data sets to other systems, locations, and/or formats in order to make the enhanced data set available to other systems. FIG. 5 is a logical block diagram illustrating data store export, according to some embodiments. Data store management request handling 214 may support via an interface requests to export data store, as indicated at 214. Export data store request 512 may include various features, such as a target data store or system, target data format, other specified operations to modify or prepare data for the target data system, selected ranges, portions, predicates, or other values used to identify a subset of the enhanced data set 514 to export from enhanced data set, whether to perform itemized or batch export (e.g., by exporting a group of items or a file or other data object of items), among other features.

Data store export 224 may implement a fetch data 510 export stage, in various embodiments. Fetch data 510 may be able to get data items 516 from enhanced data set 514 according to the export data store request 512. For example fetch data 510 may implement batch or serialized techniques for getting items in groups or individually. Fetch data 510 may implement a storage interface or driver capable of reading the items, in some embodiments, in order to provide the items to data conversion 520 in the appropriate form for data conversion 520.

In various embodiments, data store export 224 may implement data conversion 520. Data store conversion 520 may support different target formats, data stores, and/or systems. For example, data conversion 520 may support converting data from document or human readable formats (e.g., JSON files written according to FHIR or other specifications), into tabular formats, including various relational database formats, which may include operations such as converting numerical strings into the appropriate corresponding numeric data type, flattening nested records, among others. In another example, data conversion 520 may support converting enhanced data sets into data sets optimized for various machine learning systems, services, and/or techniques. For instance, an enhanced data set may be converted into a format for natural language search services implemented using machine learning models or converted into a format for training various classification or other machine learning models.

Data conversion 520 may provide converted data to store data 530 export stage. Store data 530 may obtain the appropriate access credentials, establish the appropriate network connections, utilize a proper interface or other format for storing converted items 532 in to exported set 540 into the specified storage system, service, or other location specified in export request 512. Store data 530 may implement various error handling features to ensure that failures to store items or other operations may be retried or reported, in some embodiments. Although not illustrated, various stages of data store export 224 may update corresponding state information for the request, which may be used to respond or indicate (e.g., via an interface) when the export request is complete.

Although FIGS. 2-5 have been described and illustrated in the context of a particular data store management service, the various techniques and components illustrated and described in FIGS. 2-5 may be easily applied to other data store management systems in different embodiments that may implement enhancing data sets to create data stores. Stand-alone data store management systems which may coordinate operations with services offered by different provider networks (e.g., offering other data sets or machine learning services) are an example of another embodiment that may be implemented, as well as embodiments where one or multiple components are implemented in private networks or systems to perform similar techniques to those described above. As such, FIGS. 2-5 are not intended to be limiting as to other embodiments of a system that may implement enhancing data sets to create data stores.

Various different systems and devices may implement the various methods and techniques described below, either singly or working together. For example, a data store management service such as described above with regard to FIGS. 2-5 may be configured to implement the various methods. Therefore, the above examples and or any other systems or devices referenced as performing the illustrated method, are not intended to be limiting as to other different components, modules, systems, or configurations of systems and devices.

Figure 6:
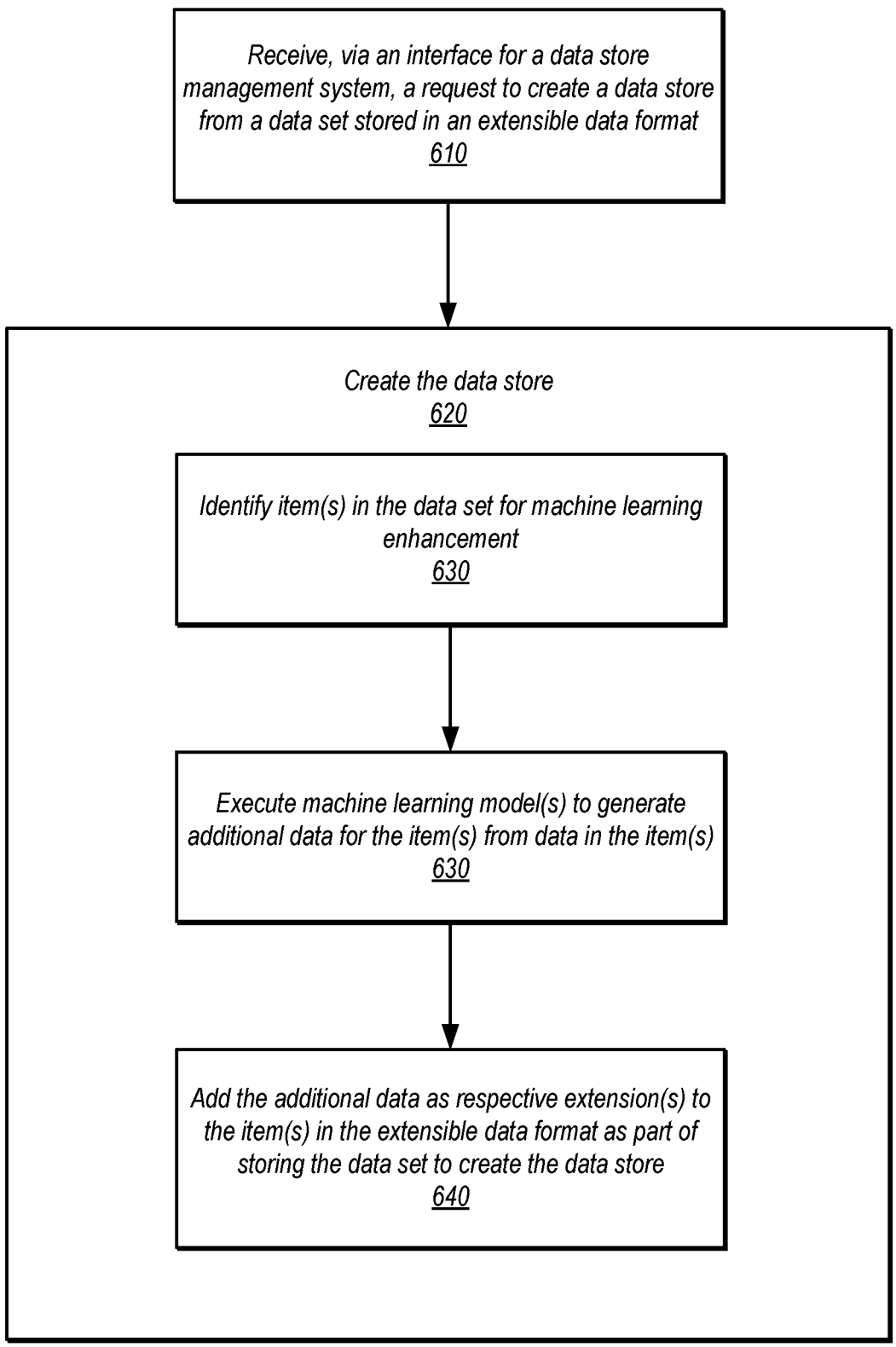
FIG. 6 is a high-level flowchart illustrating various methods and techniques to implement enhancing data sets to create data stores, according to some embodiments.
Figure 7:
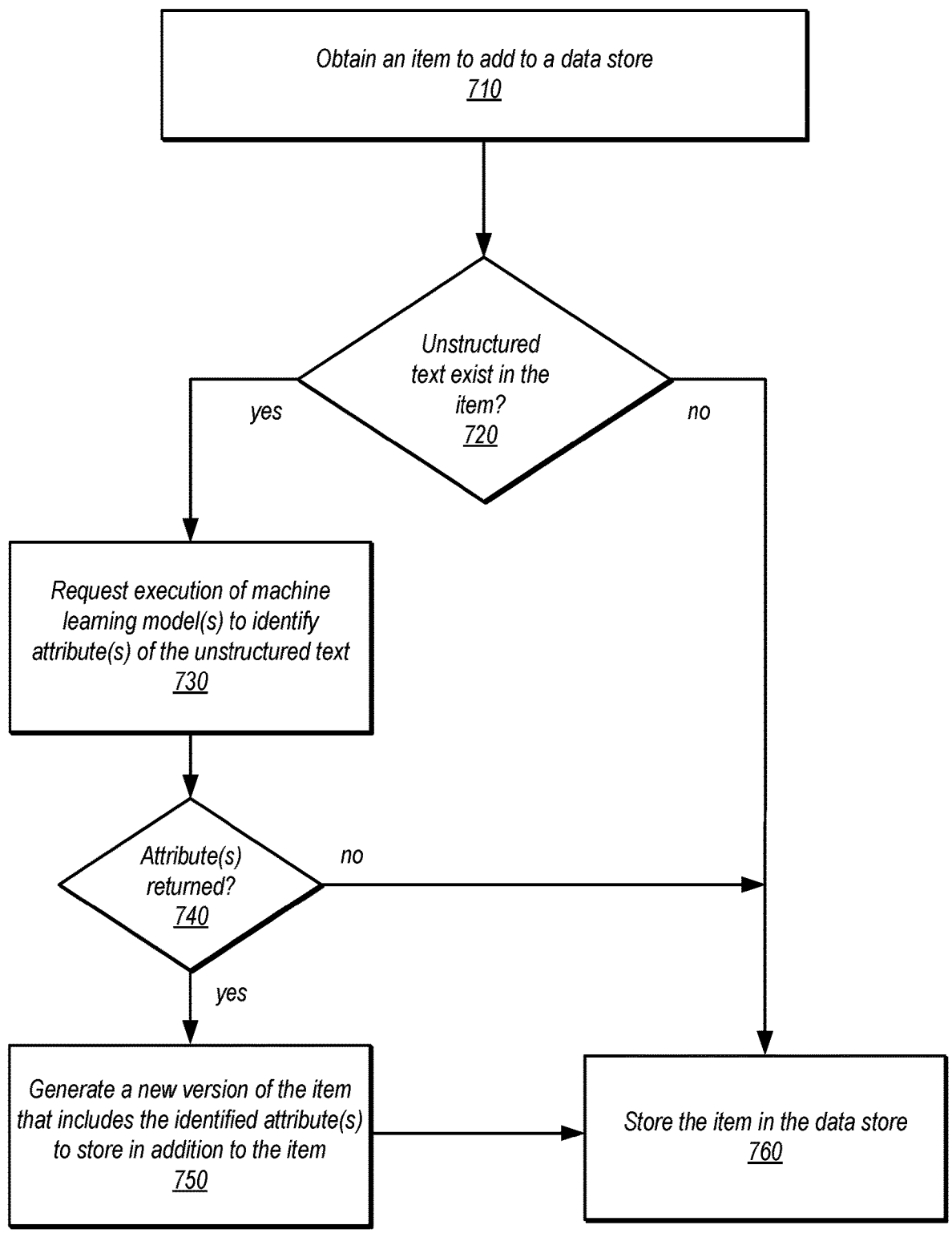
FIG. 7 is a high-level flowchart illustrating various methods and techniques to implement determining attributes for unstructured text to be added to a data store, according to some embodiments.

FIG. 6 is a high-level flowchart illustrating various methods and techniques to implement enhancing data sets to create data stores, according to some embodiments. As indicated at 610, a request to create a data store from a data set stored in an extensible data format may be received via an interface for a network-based data management service, in some embodiments. For example, various types of interfaces, programmatic (e.g., via API(s)), command line, and/or a graphical user interface (e.g., via a web-based console) may be implemented to accept data store creation requests.

Data store creation requests may include various features, as discussed above. For example, a creation request may describe a version for the data store, such as a version of the specification or other schema that describes the extensible data format (e.g., FHIR). In some embodiments, different versions of the specification may be specified so that the data may be obtained in and stored in that version of the specification or schema for the extensible data format (e.g., FHIR v. 4.0). Data store creation requests may include a name or other identifier for the data store, in some embodiments. In some embodiments, data store creation requests may include an option specify the data store to be created with pre-loaded data (e.g., instead of an empty data store which may be populated via later request). For example, a parameter or other feature of the creation request may indicate to use a default pre-loaded data set or select from multiple available pre-loaded data sets.

As indicated at 620, the data store may be created according to the request, in various embodiments. For example, various operations or tasks to create or allocate storage space, objects, or locations for metadata (e.g., for configuration information), create a workflow or other creation request tracking information, configure network, authorization, access or other controls, among other operations or tasks may be performed. As discussed above with regard to FIG. 3, items from the data set may be obtained (either individually or in batches). For example, an interpreter, parser, or other component that can read items in the data extensible format may be used to access the data set and return items which may then be stored in the data store to be created.

As discussed above with regard to FIG. 1, data enhancement may be performed for items used to create a new data store from the data set. As noted above with regard to FIG. 3 and below with regard to FIG. 7, some items may be obtained individually (e.g., as part of a create item or update item requests) for a new data store, while others may be fetched from the identified data set, in some embodiments. As indicated at 630, some item(s) from the data set may be identified for machine learning enhancement, in some embodiments. For example, in some embodiments, items may have fields, values, attributes, or tags, which may identify data for enhancement. As discussed below, feature such as unstructured text, or other indications, like a analyzable content, like links to images, documents, or other data objects, may be recognizable according to file extension, location, or various other characteristics as susceptible to enhancement by machine learning techniques. In some embodiments, the machine learning techniques for enhancement may be specified as part of the creation request, and therefore an evaluation to identify for the specified machine learning techniques may be carried out.

As indicated at 630, machine learning model(s) may be executed to generate additional data for the item(s) from data in the item(s), in some embodiments. For example, different machine learning services that perform different types of analysis may be selected according to the identified items, requests may be formatted that invoke the different machine learning services, including data from the items, and sent to the respective services. In some embodiments, the data to be evaluated by the machine learning models may be included in the items (e.g., text data). In some embodiments, the data may provide a link or location of data (e.g.,. a link to a document, image, audio, or other information) which may then be obtained by the machine learning service to perform an analysis and determine the additional data. In various embodiments, one or more portions of additional data (e.g., one or multiple labels, classifications, or other attributes) may be generated for each item. For example, unstructured text data may have multiple attribute labels created for it. In some embodiments, these labels may correspond to data types or labels of a domain of knowledge to which the extensible data format extends. For example, FHIR may support various resource types, which may be extended using a set of different data types. The additional data may correspond to one (or more) of these data types.

In some embodiments, multiple machine learning models may be executed in order to enhance data. For example, a linked document in Portable Document Format (PDF), image data, or other form may first be analyzed to recognize and extract text from the linked document. Then, a second machine learning model may be executed to identify domain-specific attributes based on the text, such as the medical information that can be recognized as discussed above with regard to FIG. 1. In some embodiments, these different machine learning models may be executed in different services. A data store management service may determine a workflow or plan of execution for the different services, execute requests according to the determined workflow and provide the output received from one service as input data in a form appropriate for invoking another service, in some embodiments.

As indicated at 640, the additional data may be added as respective extensions to the item(s) in the extensible data format as part of storing the data set to create the data store, in some embodiments. For example, as discussed below, the item(s) may be rewritten or modified to include additional fields or values. In some embodiments, data objects or files may be appended, linked, or otherwise included that store the additional data, may be stored along with the item(s). As noted below, not all item(s) may have additional data to be generated. Such items may be stored without enhancement, in some embodiments.

In various embodiments, some extensible data formats may rely upon portions which store unstructured text data, which may be susceptible to enhancement. Unstructured text may, for instance, be stored in binary from. FIG. 7 is a high-level flowchart illustrating various methods and techniques to implement determining attributes for unstructured text to be added to a data store, according to some embodiments. As indicated at 710, an item may be obtained to add to a data store, in various embodiments. For example, the item may be obtained as part of creating a data store from a pre-loaded data set, or may be obtained as part of a request to create the item in an existing data store or update the item in an existing data store.

As indicated at 720, an evaluation of the item may determine whether unstructured text exists in the item, in some embodiments. For example, a header or other metadata for the item may describe a portion (e.g., field) of the item that stores binary text data (or links to binary text data). For items that do not include unstructured text, then as indicated by the negative exit from 720, the item may be stored in the data store, as indicated at 760, in some embodiments.

For those items that do include unstructured text, then as indicated at 730, execution of machine learning model(s) to identify attribute(s) of the unstructured text may be requested, in some embodiments. For example, the unstructured text data may be provided to a natural language processing service with a model trained for a domain of knowledge specific to the data store (e.g., medical text recognition, legal text recognition, etc.). The machine learning service may return the attribute(s) determined or not, as indicated at 740. For example, in some embodiments, an error or none found response may be received, which may cause the item to be stored in the data store, as indicated by the negative exit from 740 to 760. In some embodiments, various error handling operations may also be performed (e.g., flagging the item for human review, alternative machine learning model analysis, reobtaining the item to check for data corruption errors, etc.).

For those items with attributes returned, a new version of the item may be generated that includes the identified attribute(s) to store in addition to the item, in some embodiments, as indicated at 750. For example, a copy of the item(s) may be written to include extension fields or other delimiting characters, symbols, or other information along with the attribute text. The new version of the item may then be stored in addition to the item in the data store, as indicated at 760, in various embodiments. Although techniques discussed above were performed with regard to unstructured text, similar techniques for other types of data that can be enhanced may be performed. For example, image data, audio data, tabular or other numerical data, unknown file extensions, or various other item data that can have attributes added may be evaluated by requests to execute machine learning models as well as have the respective items rewritten to include the found attributes.

The methods described herein may in various embodiments be implemented by any combination of hardware and software. For example, in one embodiment, the methods may be implemented by a computer system (e.g., a computer system as in FIG. 8) that includes one or more processors executing program instructions stored on a computer-readable storage medium coupled to the processors. The program instructions may be configured to implement the functionality described herein (e.g., the functionality of various servers and other components that implement the network-based virtual computing resource provider described herein). The various methods as illustrated in the figures and described herein represent example embodiments of methods. The order of any method may be changed, and various elements may be added, reordered, combined, omitted, modified, etc.

Figure 8:
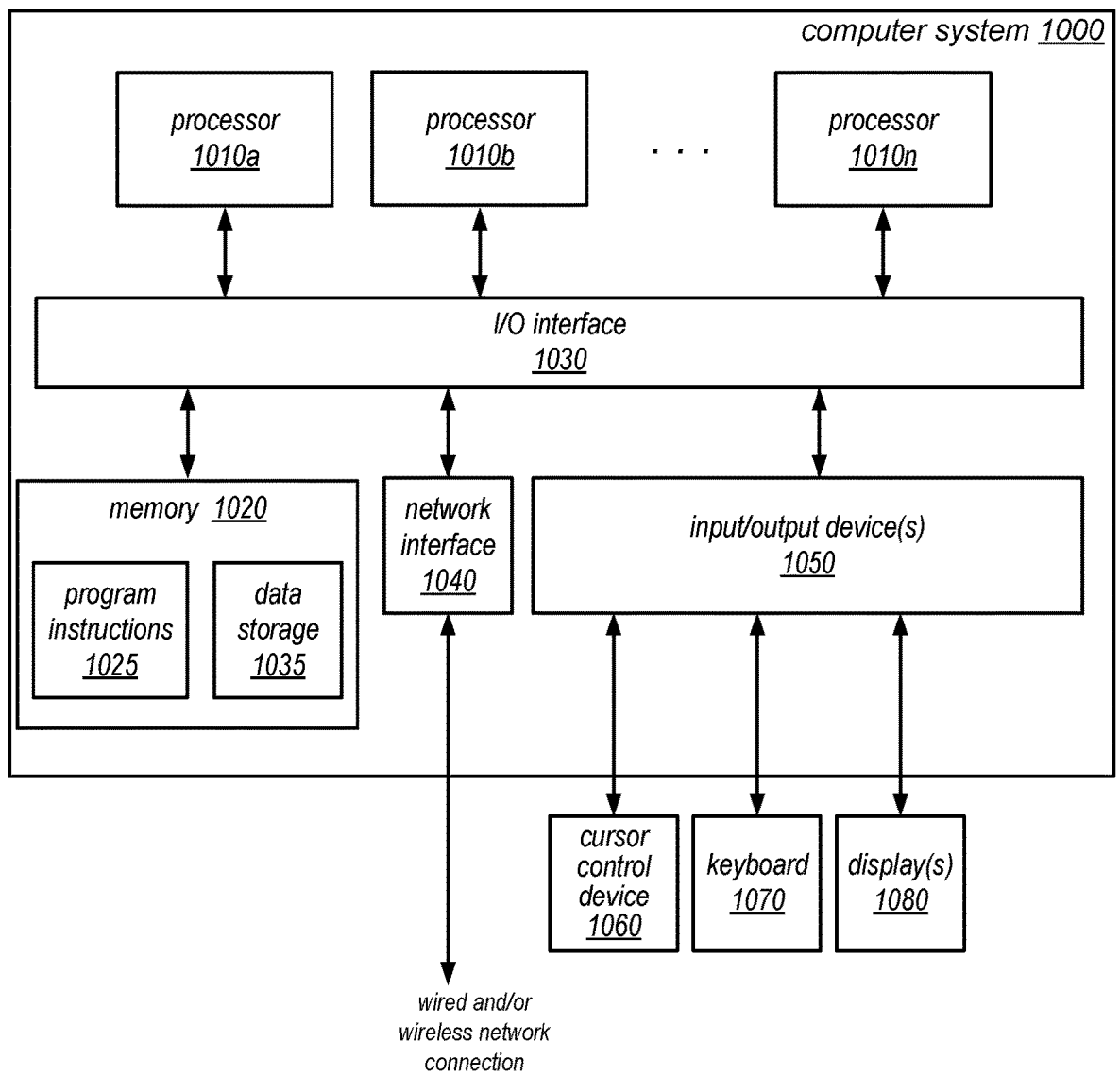
FIG. 8 illustrates an example system configured to implement the various methods, techniques, and systems described herein, according to some embodiments.

Embodiments of enhancing data sets to create data stores as described herein may be executed on one or more computer systems, which may interact with various other devices. One such computer system is illustrated by FIG. 8. In different embodiments, computer system 1000 may be any of various types of devices, including, but not limited to, a personal computer system, desktop computer, laptop, notebook, or netbook computer, mainframe computer system, handheld computer, workstation, network computer, a camera, a set top box, a mobile device, a consumer device, video game console, handheld video game device, application server, storage device, a peripheral device such as a switch, modem, router, or in general any type of compute node, computing device, or electronic device.

In the illustrated embodiment, computer system 1000 includes one or more processors 1010 coupled to a system memory 1020 via an input/output (I/O) interface 1030. Computer system 1000 further includes a network interface 1040 coupled to I/O interface 1030, and one or more input/output devices 1050, such as cursor control device 1060, keyboard 1070, and display(s) 1080. Display(s) 1080 may include standard computer monitor(s) and/or other display systems, technologies or devices. In at least some implementations, the input/output devices 1050 may also include a touch- or multi-touch enabled device such as a pad or tablet via which a user enters input via a stylus-type device and/or one or more digits. In some embodiments, it is contemplated that embodiments may be implemented using a single instance of computer system 1000, while in other embodiments multiple such systems, or multiple nodes making up computer system 1000, may be configured to host different portions or instances of embodiments. For example, in one embodiment some elements may be implemented via one or more nodes of computer system 1000 that are distinct from those nodes implementing other elements.

In various embodiments, computer system 1000 may be a uniprocessor system including one processor 1010, or a multiprocessor system including several processors 1010 (e.g., two, four, eight, or another suitable number). Processors 1010 may be any suitable processor capable of executing instructions. For example, in various embodiments, processors 1010 may be general-purpose or embedded processors implementing any of a variety of instruction set architectures (ISAs), such as the x86, PowerPC, SPARC, or MIPS ISAs, or any other suitable ISA. In multiprocessor systems, each of processors 1010 may commonly, but not necessarily, implement the same ISA.

In some embodiments, at least one processor 1010 may be a graphics processing unit. A graphics processing unit or GPU may be considered a dedicated graphics-rendering device for a personal computer, workstation, game console or other computing or electronic device. Modern GPUs may be very efficient at manipulating and displaying computer graphics, and their highly parallel structure may make them more effective than typical CPUs for a range of complex graphical algorithms. For example, a graphics processor may implement a number of graphics primitive operations in a way that makes executing them much faster than drawing directly to the screen with a host central processing unit (CPU). In various embodiments, graphics rendering may, at least in part, be implemented by program instructions configured for execution on one of, or parallel execution on two or more of, such GPUs. The GPU(s) may implement one or more application programmer interfaces (APIs) that permit programmers to invoke the functionality of the GPU(s). Suitable GPUs may be commercially available from vendors such as NVIDIA Corporation, ATI Technologies (AMD), and others.

System memory 1020 may be configured to store program instructions and/or data accessible by processor 1010. In various embodiments, system memory 1020 may be implemented using any suitable memory technology, such as static random access memory (SRAM), synchronous dynamic RAM (SDRAM), nonvolatile/Flash-type memory, or any other type of memory. In the illustrated embodiment, program instructions and data implementing desired functions, such as those described above are shown stored within system memory 1020 as program instructions 1025 and data storage 1035, respectively. In other embodiments, program instructions and/or data may be received, sent or stored upon different types of computer-accessible media or on similar media separate from system memory 1020 or computer system 1000. Generally speaking, a non-transitory, computer-readable storage medium may include storage media or memory media such as magnetic or optical media, e.g., disk or CD/DVD-ROM coupled to computer system 1000 via I/O interface 1030. Program instructions and data stored via a computer-readable medium may be transmitted by transmission media or signals such as electrical, electromagnetic, or digital signals, which may be conveyed via a communication medium such as a network and/or a wireless link, such as may be implemented via network interface 1040.

In one embodiment, I/O interface 1030 may be configured to coordinate I/O traffic between processor 1010, system memory 1020, and any peripheral devices in the device, including network interface 1040 or other peripheral interfaces, such as input/output devices 1050. In some embodiments, I/O interface 1030 may perform any necessary protocol, timing or other data transformations to convert data signals from one component (e.g., system memory 1020) into a format suitable for use by another component (e.g., processor 1010). In some embodiments, I/O interface 1030 may include support for devices attached through various types of peripheral buses, such as a variant of the Peripheral Component Interconnect (PCI) bus standard or the Universal Serial Bus (USB) standard, for example. In some embodiments, the function of I/O interface 1030 may be split into two or more separate components, such as a north bridge and a south bridge, for example. In addition, in some embodiments some or all of the functionality of I/O interface 1030, such as an interface to system memory 1020, may be incorporated directly into processor 1010.

Network interface 1040 may be configured to allow data to be exchanged between computer system 1000 and other devices attached to a network, such as other computer systems, or between nodes of computer system 1000. In various embodiments, network interface 1040 may support communication via wired or wireless general data networks, such as any suitable type of Ethernet network, for example; via telecommunications/telephony networks such as analog voice networks or digital fiber communications networks; via storage area networks such as Fibre Channel SANs, or via any other suitable type of network and/or protocol.

Input/output devices 1050 may, in some embodiments, include one or more display terminals, keyboards, keypads, touchpads, scanning devices, voice or optical recognition devices, or any other devices suitable for entering or retrieving data by one or more computer system 1000. Multiple input/output devices 1050 may be present in computer system 1000 or may be distributed on various nodes of computer system 1000. In some embodiments, similar input/output devices may be separate from computer system 1000 and may interact with one or more nodes of computer system 1000 through a wired or wireless connection, such as over network interface 1040.

As shown in FIG. 8, memory 1020 may include program instructions 1025, configured to implement the various methods and techniques as described herein, and data storage 1035, comprising various data accessible by program instructions 1025. In one embodiment, program instructions 1025 may include software elements of embodiments as described herein and as illustrated in the Figures. Data storage 1035 may include data that may be used in embodiments. In other embodiments, other or different software elements and data may be included.

Those skilled in the art will appreciate that computer system 1000 is merely illustrative and is not intended to limit the scope of the techniques as described herein. In particular, the computer system and devices may include any combination of hardware or software that can perform the indicated functions, including a computer, personal computer system, desktop computer, laptop, notebook, or netbook computer, mainframe computer system, handheld computer, workstation, network computer, a camera, a set top box, a mobile device, network device, internet appliance, PDA, wireless phones, pagers, a consumer device, video game console, handheld video game device, application server, storage device, a peripheral device such as a switch, modem, router, or in general any type of computing or electronic device. Computer system 1000 may also be connected to other devices that are not illustrated, or instead may operate as a stand-alone system. In addition, the functionality provided by the illustrated components may in some embodiments be combined in fewer components or distributed in additional components. Similarly, in some embodiments, the functionality of some of the illustrated components may not be provided and/or other additional functionality may be available.

Those skilled in the art will also appreciate that, while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a non-transitory, computer-accessible medium separate from computer system 1000 may be transmitted to computer system 1000 via transmission media or signals such as electrical, electromagnetic, or digital signals, conveyed via a communication medium such as a network and/or a wireless link. Various embodiments may further include receiving, sending or storing instructions and/or data implemented in accordance with the foregoing description upon a computer-accessible medium. Accordingly, the present invention may be practiced with other computer system configurations.

It is noted that any of the distributed system embodiments described herein, or any of their components, may be implemented as one or more web services. For example, nodes within a data lineage system may present data lineage services to clients as network-based services. In some embodiments, a network-based service may be implemented by a software and/or hardware system designed to support interoperable machine-to-machine interaction over a network. A network-based service may have an interface described in a machine-processable format, such as the Web Services Description Language (WSDL). Other systems may interact with the web service in a manner prescribed by the description of the network-based service's interface. For example, the network-based service may define various operations that other systems may invoke, and may define a particular application programming interface (API) to which other systems may be expected to conform when requesting the various operations.

In various embodiments, a network-based service may be requested or invoked through the use of a message that includes parameters and/or data associated with the network-based services request. Such a message may be formatted according to a particular markup language such as Extensible Markup Language (XML), and/or may be encapsulated using a protocol such as Simple Object Access Protocol (SOAP). To perform a web services request, a network-based services client may assemble a message including the request and convey the message to an addressable endpoint (e.g., a Uniform Resource Locator (URL)) corresponding to the web service, using an Internet-based application layer transfer protocol such as Hypertext Transfer Protocol (HTTP).

In some embodiments, web services may be implemented using Representational State Transfer ("RESTful") techniques rather than message-based techniques. For example, a web service implemented according to a RESTful technique may be invoked through parameters included within an HTTP method such as PUT, GET, or DELETE, rather than encapsulated within a SOAP message.

The various methods as illustrated in the FIGS. and described herein represent example embodiments of methods. The methods may be implemented in software, hardware, or a combination thereof. The order of method may be changed, and various elements may be added, reordered, combined, omitted, modified, etc.

Various modifications and changes may be made as would be obvious to a person skilled in the art having the benefit of this disclosure. It is intended that the invention embrace all such modifications and changes and, accordingly, the above description to be regarded in an illustrative rather than a restrictive sense.

What is claimed is:

1. A system, comprising:
  at least one processor; and
  a memory, storing program instructions that when executed by the at least one processor, cause the at least one processor to:
    receive, via an interface of a network-based data store management service, a request to create a data store from a pre-loaded data set stored in an extensible data format;
    responsive to the request, create the data store in the network-based data store management service, wherein to create the data store, the program instructions cause the at least one processor to:
      identify one or more items in the data set for machine learning enhancement according to data in the one or more items that references one more data objects;
      obtain the one or more data objects according to the data that references the one or more data objects;
      generate a plan to generate additional data descriptive of the one or more data objects referenced in the data in the one or more data objects, wherein the plan comprises an order to execute two or more machine learning models to generate additional data descriptive of the one or more data objects referenced in the data;
      execute the plan to generate the additional data by causing execution of the two or more machine learning models in the order using output of a first one of the two or more machine learning models as input to a second one of the two or more machine learning models using the obtained one or more data objects as input to at least one of the two or more machine learning models, wherein the two or more machine learning models are selected based on the identified one or more items in the data set for machine learning enhancement;
      store, in the one or more items, the additional data descriptive of the one or more data objects referenced in the data generated by the two or more machine learning models as respective extensions to the one or more items in the extensible data format as part of storing the data set in the data store; and
    send a response to the request indicating that the data store is created.

2. The system of claim 1, wherein the memory stores further program instructions that when executed by the at least one processor, cause the at least one processor to:
  receive, via the interface, a request to export the data store to a target location; and
  convert, by the network-based data store management service, the one or more items extended with the additional data into a different data format as part of exporting the data store to the target location.

3. The system of claim 1, wherein a further one or more items in the data set are identified for machine learning enhancement based, at least in part, on portions of the further one or more items storing unstructured text, and wherein further additional data is determined for the further one or more data items that comprises one or more attributes that describe the unstructured text.

4. The system of claim 1, wherein the data set comprises a plurality of synthetically generated healthcare records.

5. A method, comprising:
  receiving, via an interface of a data store management system, a request to create a data store from a data set stored in an extensible data format;
  creating, by the data store management system, the data store, comprising:
    identifying one or more items in the data set for machine learning enhancement according to data in the one or more items that references one more data objects;
    obtaining the one or more data objects according to the data that references the one or more data objects;
    generating a plan to generate additional data descriptive of the one or more data objects referenced in the data in the one or more data objects, wherein the plan comprises an order to execute two or more machine learning models to generate additional data descriptive of the one or more data objects referenced in the data, wherein the two or more machine learning models are selected based on the identified one or more items in the data set for machine learning enhancement;

executing the plan to generate the additional data by causing execution of the two or more machine learning models in the order using output of a first one of the two or more machine learning models as input to a second one of the two or more machine learning models using the obtained one or more data objects as input to at least one of the two or more machine learning models; and storing, in the one or more items, the additional data descriptive of the one or more data objects referenced in the data generated by the two or more machine learning models as respective extensions to the one or more items in the extensible data format as part of storing the data set in the data store.

6. The method of claim 5, further comprising:
receiving, via the interface, a request to export the data store to a target location; and
converting, by the data store management system, the one or more items extended with the additional data into a different data format as part of exporting the data store to the target location.

7. The method of claim 5, further comprising:
receiving, via the interface, a request to create a new item in the data store;
executing, by the data store management system, the at least one of the two or more learning models to generate additional data for the new item; and
adding, by the data store management system, the additional data as an extension to the new item as part of storing the new item in the data store.

8. The method of claim 5, wherein a version of the extensible data format is specified in the request to create the data store.

9. The method of claim 5, wherein executing the plan to generate the additional data comprises sending different requests to different machine learning services to obtain the additional data, wherein at least one of the different requests include individual ones of the one or more data objects.

10. The method of claim 5, wherein a search index is created for the data store as part of creating the data store and wherein the method further comprises:
receiving, via the interface for the data store management system, a search request for the data store; and
returning, via the interface, a result for the search request based on an evaluation of the search request using the search index, wherein the result includes at least some of the additional data generated for the one or more items.

11. The method of claim 5, wherein executing the plan to generate the additional data comprises obtaining output generated by execution of the first one of the one or more machine learning models and sending the output as input as part of a request for the execution of the second one of the one or more machine learning models.

12. The method of claim 5, wherein a further one or more items in the data set are identified for machine learning enhancement based, at least in part, on identifying portions of the further one or more items as storing unstructured text, and wherein further additional data is generated that comprises one or more attributes that describe the unstructured text.

13. The method of claim 5, wherein the data set is a pre-loaded data set that was synthetically generated for the data store management system.

14. One or more non-transitory, computer-readable storage media, storing program instructions that when executed on or across one or more computing devices cause the one or more computing devices to implement:
receiving, via an interface of a network-based data store management service, a request to create a data store from a data set previously stored in the network-based data store management service in an extensible data format;
responsive to the request, creating the data store, wherein in creating the data store the program instructions cause the one or more computing devices to implement:
identifying one or more items in the data set for machine learning enhancement according to data in the one or more items that references one more data objects;
obtaining the one or more data objects according to the data that references the one or more data objects;
generating a plan to generate additional data descriptive of the one or more data objects referenced in the data in the one or more data objects, wherein the plan comprises an order to execute two or more machine learning models to generate additional data descriptive of the one or more data objects referenced in the data, wherein the two or more machine learning models are selected based on the identified one or more items in the data set for machine learning enhancement;
executing the plan to generate the additional data by causing execution of the two or more machine learning models in the order using output of a first one of the two or more machine learning models as input to a second one of the two or more machine learning models using the obtained one or more data objects as input to at least one of the two or more machine learning models; and
storing, in the one or more items, the additional data descriptive of the one or more data objects referenced in the data generated by the two or more machine learning models as respective extensions to the one or more items in the extensible data format as part of storing the data set in the data store.

15. The one or more non-transitory, computer-readable storage media of claim 14, storing further instructions that when executed by the one or more computing devices, cause the one or more computing devices to further implement:
receiving, via the interface, a request to export the data store to a target location; and
converting, by the network-based data store management service, the one or more items extended with the additional data into a different data format as part of exporting the data store to the target location.

16. The one or more non-transitory, computer-readable storage media of claim 14, wherein, in causing the execution of the plan to generate the additional data, program instructions cause the one or more computing devices to implement sending different requests to different machine learning services to cause the execution of the two or more machine learning models.

17. The one or more non-transitory, computer-readable storage media of claim 14, wherein a search index is created for the data store as part of creating the data store and wherein the one or more non-transitory, computer-readable storage media store further instructions that when executed by the one or more computing devices, cause the one or more computing devices to further implement:
  receiving, via the interface for the network-based data store management service, a search request for the data store; and
  returning, via the interface, a result for the search request based on an evaluation of the search request using the search index, wherein the result includes at least some of the additional data generated for the one or more items.

18. The one or more non-transitory, computer-readable storage media of claim 14, wherein a further one or more items in the data set are identified for machine learning enhancement based, at least in part, on identifying portions of the further one or more items as storing unstructured text, and wherein further additional data is generated that comprises one or more attributes that describe the unstructured text.

19. The one or more non-transitory, computer-readable storage media of claim 14, storing further instructions that when executed by the one or more computing devices, cause the one or more computing devices to further implement:
  after creating the data store, sending, via the interface of the network-based data store management service, an indication that the data store is created.

20. The one or more non-transitory, computer-readable storage media of claim 14, wherein the data set comprises a plurality of synthetically generated healthcare records.

* * * * *